United States Patent [19]
Payne et al.

[11] Patent Number: 5,807,701
[45] Date of Patent: Sep. 15, 1998

[54] METHOD AND APPARATUS FOR DETECTING MICROORGANISMS

[75] Inventors: Peter Alfred Payne, Bramhall; Krishna Chandra Persaud, Chorlton, both of United Kingdom

[73] Assignee: Aromascan PLC, Crewe, United Kingdom

[21] Appl. No.: 750,652

[22] PCT Filed: Jun. 9, 1995

[86] PCT No.: PCT/GB95/01347

§ 371 Date: Feb. 28, 1997

§ 102(e) Date: Feb. 28, 1997

[87] PCT Pub. No.: WO95/33848

PCT Pub. Date: Dec. 14, 1995

[30] Foreign Application Priority Data

Jun. 9, 1994 [GB] United Kingdom ................. 9411515

[51] Int. Cl.$^6$ .............. C12Q 1/04; C12Q 1/00; G01N 7/00; G01N 30/96

[52] U.S. Cl. .............. 435/34; 435/4; 435/300.1; 435/807; 435/283.1; 435/287.1; 435/287.5; 435/286.6; 435/285.2; 422/50; 422/83; 422/88

[58] Field of Search ................ 435/34, 4, 300.1, 435/807, 283.1, 287.1, 287.5, 286.6, 285.2; 422/50, 83, 88

[56] References Cited

U.S. PATENT DOCUMENTS

| 4,246,343 | 1/1981 | Wilkins et al. | 435/34 |
|---|---|---|---|
| 4,386,157 | 5/1983 | Nishioka et al. | 435/34 |
| 5,051,360 | 9/1991 | Waters | 435/34 |
| 5,094,955 | 3/1992 | Calandra et al. | 435/34 |
| 5,164,796 | 11/1992 | Di Guiseppi et al. | 435/34 |

FOREIGN PATENT DOCUMENTS

| 124193 | 11/1984 | European Pat. Off. | C12M 1/34 |
|---|---|---|---|
| 158497 | 10/1985 | European Pat. Off. | C12Q 1/02 |
| 0264221 | 4/1988 | European Pat. Off. | |
| 286307B | 11/1993 | European Pat. Off. | |
| 0597584 | 5/1994 | European Pat. Off. | |
| 60-130398 | 7/1985 | Japan . | |
| WO9013663 | 5/1989 | WIPO | C12Q 1/04 |
| WO9404705 | 3/1994 | WIPO . | |

OTHER PUBLICATIONS

Shen–Wu Ho, "Head–Space Gas–Liquid Chromatrographic Analysis for Presumptive Identification of Bacteria in Blood Cultures", Feb. 1986, pp. 18–26.

Gardner et al., "A brief history of electronic noses" *Sensors and Actuators B. 18–19* (1994), pp. 211–220 Month not available.

J.L. Berdagué et al., "Revue Caractérisation Instrumentale De La Qualité Des Matiéres Premiéres Et Des Aliments Par Analyse Des Composés Volatils", Viandes Prod. Carnés vol. 14, Sep.–Oct. 1993, pp. 135–138; (with English language summary).

M. Sasser, "Identification of Bacteria by Gas Chromatography of Cellular Fatty Acids", Technical Note #101, MIDI, May 1990, pp. 163–169.

M. Sasser, "'Tracking' a Strain Using the Microbial Identification System", Technical Note #102, MIDI, May 1990, pp. 171–174.

Primary Examiner—Louise N. Leary
Attorney, Agent, or Firm—Christie, Parker & Hale, LLP

[57] ABSTRACT

A method for identifying a microorganism is described that includes abstracting gas or vapor associated with the microorganism from a detection region and flowing the same over an array of sensors of which an electrical property varies according to exposure to gases or vapors and observing the response of the sensors. An apparatus for detecting a microorganism is also disclosed having a detector means for detecting a gas or vapor associated with the microorganism which includes an array of sensors of which an electrical property varies according to exposure to the gases or vapors.

48 Claims, 2 Drawing Sheets

METHOD AND APPARATUS FOR DETECTING MICROORGANISMS

This invention relates to detecting bacteria.

Bacteria are identified in a variety of ways. Many have characteristic forms which can be seen under microscopic examination, but some are identified, when colonised on a growth medium, by a characteristic colour and in some cases this is confirmed by smell. Not all bacteria have any appreciable odour, but many have a characteristic associated gas or vapour due to their inherent metabolic activities.

Patent Abstracts of Japan, application number JP-A-60130398, discloses a detector for detecting the presence of microorganisms on the basis of evolved gases. WO 94/04705 discloses a method of detecting *E. Coli* by monitoring a gaseous product, this gaseous product being produced by cleavage of a glucuronide conjugate by β-glucuronidase produced by a certain bacterial species. GB-A-2176901 describes gas sensors based on the use of semi-conducting organic polymers, whilst U.S. Pat. No. 4,456,380 discloses an optical bacteria identification system using a plurality of optical filters.

The invention comprises a method for identifying bacteria comprising detecting gas or vapour associated with the metabolic activity of the bacteria and differentiating such gas or vapour from gas or vapour associated with other bacteria.

The method may comprise abstracting gas or vapour from a detection region and flowing the same over an array of sensors of which an electrical property varies according to exposure to gases or vapours and observing the response of the sensors.

The sensors may comprise semi-conducting polymers the resistance or impedance of which varies according to exposure to gases or vapours.

The response of the sensors may be compared against a library of responses to known bacteria, or the response may be input to a neural net trained against known bacteria.

The detection region may comprise an enclosed space above a Petri dish or like laboratory culture dish.

The array of sensors may first be purged using a purging gas.

The invention also comprises apparatus for detecting bacteria comprising detector means for detecting a gas or vapour associated with the bacteria.

Said detector means may comprise an array of sensors of which an electrical property varies according to exposure to gases or vapours. The sensors may comprise semi-conducting polymers the resistance or impedance of which varies according to exposure to gases or vapours.

The apparatus may comprise a store for a library of responses to known bacteria and comparison means operable automatically to compare a given response against the library. The apparatus may also comprise a neural net the input to which comprises the array of sensors and which is trained against known bacteria.

The apparatus may comprise a probe for sampling a detection region by abstracting gas or vapour from said region to be passed to said detector means. Said probe may comprise a cover for enclosing a Petri or like laboratory culture dish or an area of growth medium thereon.

Said probe may comprise a carrier gas feed and return and the apparatus may comprise a source of carrier gas.

Embodiments of apparatus and methods for detecting bacteria according to the invention will now be described with reference to the accompanying drawings, in which.

The drawings illustrate methods and apparatus for detecting bacteria comprising detecting gas or vapour associated with the bacteria, and, further, methods for identifying bacteria by differentiating such gas or vapour from gas or vapour associated with other bacteria.

Figure 3:
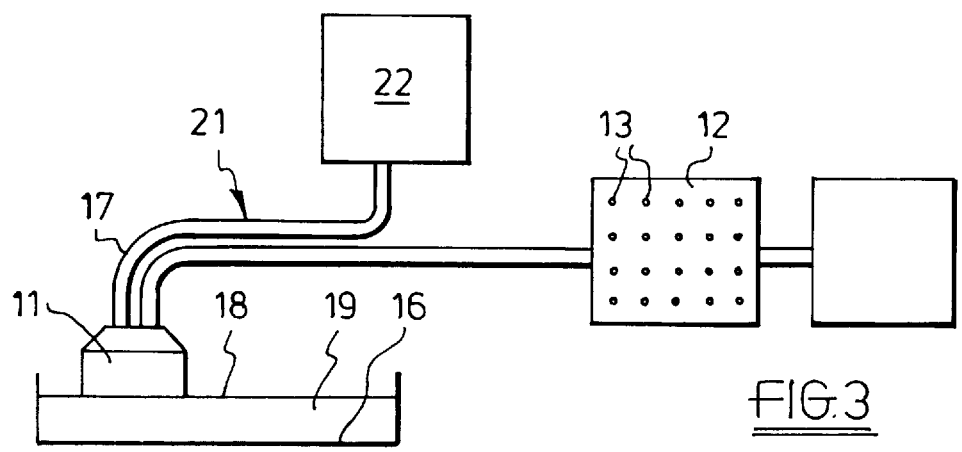
FIG. 3 is a diagrammatic illustration of an arrangement for detecting bacteria on a culture dish.
Figure 4:
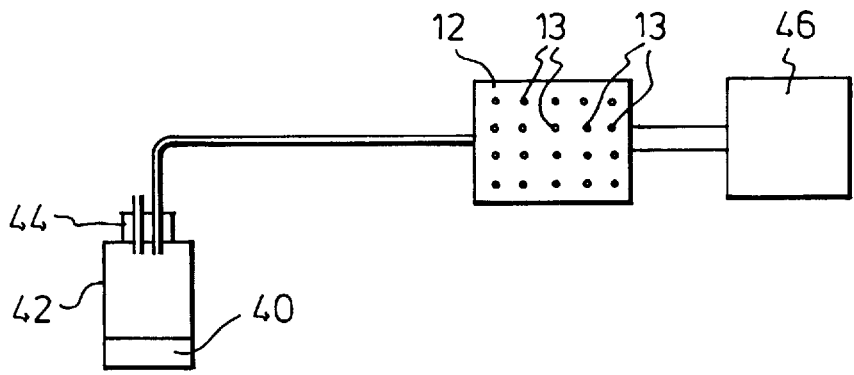
FIG. 4 is a diagrammatic illustration of an arrangement for detecting bacteria in a nutrient broth.

FIGS. 3 and 4 illustrate abstracting gas or vapour from a detection region 11 and flowing the same over an array 12 of sensors 13 of which an electrical property varies according to exposure to gases or vapours and observing the response of the sensors 13.

The sensors 13 comprise semi-conducting polymers the resistance or impedance of which varies according to exposure to gases or vapours.

An array 12 of twenty sensors has been employed to distinguish the vapours associated with the bacteria *Straphylococcus aureus, Eschericia coli* and *Group A beta-haemolytic streptococci*.

Eight epidermiologically unrelated patient isolates of each species were recovered from frozen storage. Each bacteria isolate was cultured overnight in nutrient broth 40 in a glass Duran bottle 42 with a GL-45 screw cap. After overnight incubation at 37° C. the cap was changed for a cap 44 with inlet and outlet ports. After a period of equilibration at 37° C. the headspace vapour above the broth 40 was analysed by pumping same across the 20 sensor array 12 at a flow rate of ~150 ml min$^{-1}$.

Figure 5:
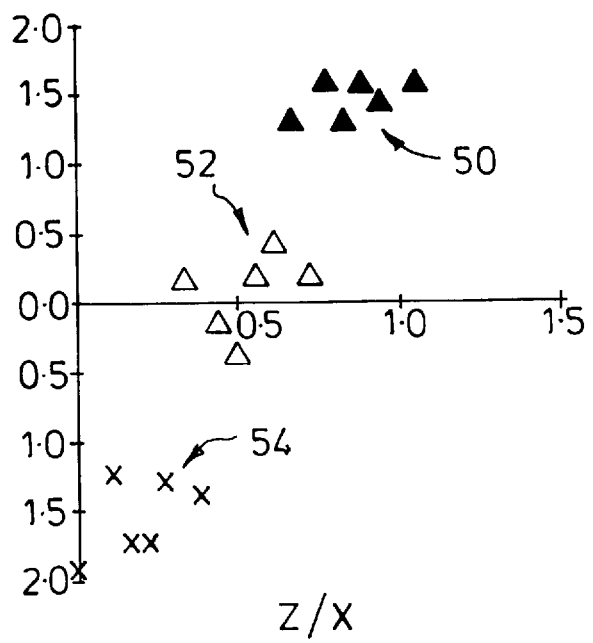
FIG. 5 is a cluster analysis of vapour associated with three species of bacteria.

The outputs of the sensors 13 were analysed by computing means 46 employing the non-linear cluster analysis mapping technique of Sammon (Sammon Jr., J. W., IEEE Trans. on computers, Vol. C-18, No. 5, May 1969, pp 401–409). FIG. 5 shows the results of this analysis, indicating that excellent separation is achieved between the clusters 50, 52, 54 associated with *Straphylococcus aureus, Eschericia coli* and *Group A beta-haemolytic streptococci* respectively.

Figure 1:
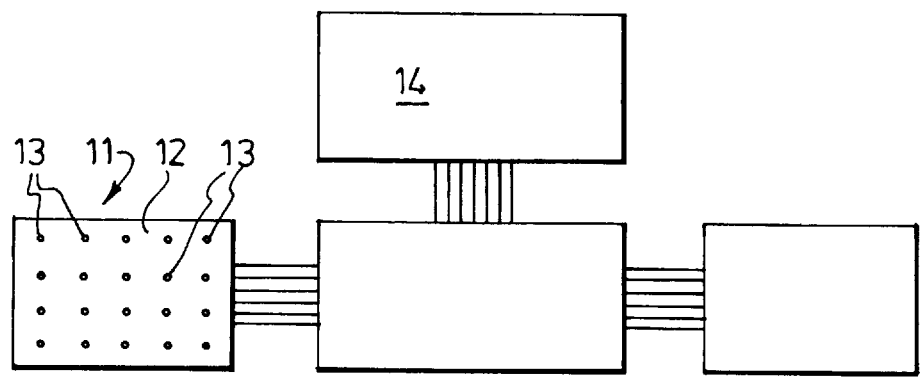
FIG. 1 is a diagrammatic illustration of a first embodiment.
Figure 2:
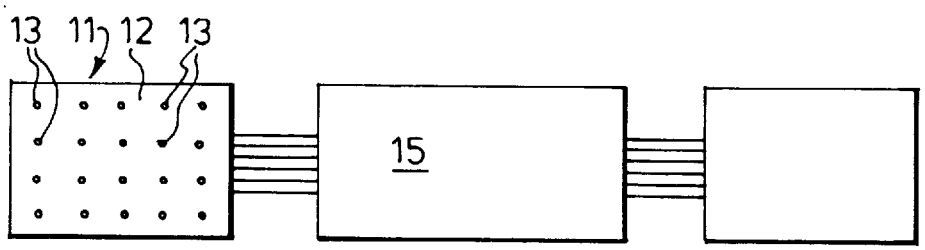
FIG. 2 is a diagrammatic illustration of a second embodiment.

FIG. 1 illustrates comparing the response of the sensors 13 against a library 14 of responses to known bacteria. FIG. 2 illustrates inputting the response to a neural net 15 trained against known bacteria.

FIG. 3 illustrates a further sampling arrangement wherein the detection region 11 comprises an enclosed space above a Petri dish 16 or like laboratory culture dish. A probe 17 comprises a cover for enclosing an area of bacterial growth 18 on a growth medium 19 in the dish 16.

The probe 17 comprises a carrier gas feed 21 feeding a carrier gas such for example as purified air or nitrogen. Prior to taking gas or vapour from a sample in, say, a Petri dish, the array 12 of sensors 13 is first purged of any residual substances from a previous sensing operation by directing over the sensors 13 a stream of purging gas, which, in this instance, is the same as the carrier gas. The gas is supplied from a pressure bottle 22.

The sensors 13 can be selected for sensitivity to a broad spectrum of gases or vapours associated with bacteria and the apparatus may also be arranged to indicate concentration by measuring the level of response. A broader spectrum and a greater sensitivity will be obtained from a given array size by using a.c. technology as taught in EP-B-0 286 307 than by simply measuring d.c. resistance.

In addition to bacteria, the method may be applied to the detection of microfungi.

It may be important to specify the state of the microorganism when making an observation. Gases or vapours associated with growing bacteria or microfungi may well be different from gases or vapours associated with the same organism in growth-arrest stage or when it has been weakened or killed.

However, the library may contain data on the gases or vapours associated with microorganisms in all possible states, or the neural net trained to recognise them, so the apparatus may also identify the state as well as the microorganism.

We claim:

1. A method for identifying a microorganism, comprising abstracting gas or vapor associated with the microorganism from a detection region and flowing the same over an array of sensors of which an electrical property varies according to exposure to gases or vapors and observing the response of the sensors.

2. The method according to claim 1, in which the sensors comprise semi-conducting polymers, the resistance or impedance of which varies according to exposure to gases or vapors.

3. The method according to claim 1 or claim 2, comprising comparing the response of the sensors against a library of responses to known microorganisms.

4. The method according to claim 1 or claim 2, comprising inputting the response to a neural net trained against known microorganisms.

5. The method according to claim 1 or claim 2, comprising performing a cluster analysis mapping of the sensor outputs.

6. The method according to claims 1 or 2, in which the detection region comprises an enclosed space above a Petri dish or other laboratory culture dish.

7. The method according to claims 1 or 2, in which the array of sensors is first purged using a purging gas.

8. An apparatus for detecting a microorganism, comprising a detector means for detecting a gas or vapor associated with the microorganism, said detector means comprising an array of sensors of which an electrical property varies according to exposure to the gases or vapors.

9. The apparatus according to claim 8, in which the sensors comprise semi-conducting polymers, the resistance or impedance of which varies according to exposure to gases or vapors.

10. The apparatus according to claim 8 or claim 9, comprising a store for a library of responses to known microorganisms and comparison means operable automatically to compare a given response against the library.

11. The apparatus according to claim 8 or claim 9, comprising a neural net, the input to which comprises the array of sensors and which is trained against known microorganisms.

12. The apparatus according to claims 8 or 9, comprising a probe for sampling a detection region by abstracting gas or vapor from said region to be passed to said detector means.

13. The apparatus according to claim 12, said probe comprising a cover for enclosing a Petri or other laboratory dish or an area of growth medium thereon.

14. The apparatus according to claim 13, said probe comprising a carrier gas feed and return.

15. The apparatus according to claim 14, comprising a source of carrier gas.

16. The method according to claim 1, wherein the microorganism is a bacteria.

17. The method according to claim 16, in which the sensors comprise semi-conducting polymers, the resistance or impedance of which varies according to exposure to gases or vapors.

18. The method according to claim 16 or claim 17, comprising comparing the response of the sensors against a library of responses to known bacteria.

19. The method according to claim 16 or claim 17, comprising inputting the response to a neural net trained against known bacteria.

20. The method according to claim 16 or claim 17, comprising performing a cluster analysis mapping of the sensor outputs.

21. The method according to claim 16 or claim 17, in which the detection region comprises an enclosed space above a Petri dish or other laboratory culture dish.

22. The method according to any one of claim 16 or claim 17, in which the array of sensors is first purged using a purging gas.

23. The apparatus according to claim 8, wherein the microorganism is a bacteria.

24. The apparatus according to claim 23, in which the sensors comprise semi-conducting polymers, the resistance or impedance of which varies according to exposure to gases or vapors.

25. The apparatus according to claim 23 or claim 24, comprising a store for a library of responses to known bacteria and comparison means operable automatically to compare a given response against the library.

26. The apparatus according to claim 23 or claim 24, comprising a neural net, the input to which comprises the array of sensors and which is trained against known bacteria.

27. The apparatus according to claim 23 or 24, comprising a probe for sampling a detection region by abstracting gas or vapor from said region to be passed to said detector means.

28. The apparatus according to claim 27, said probe comprising a cover for enclosing a Petri or other laboratory culture dish or an area of growth medium thereon.

29. The apparatus according to claim 28, said probe comprising a carrier gas feed and return.

30. The apparatus according to claim 29, comprising a source of carrier gas.

31. The method according to claim 1, wherein the microorganism is a microfungi.

32. The method according to claim 31, in which the sensors comprise semi-conducting polymers, the resistance or impedance of which varies according to exposure to gases or vapors.

33. The method according to claim 31 or claim 32, comprising comparing the response of the sensors against a library of responses to known microfungi.

34. The method according to claim 31 or claim 32, comprising inputting the response to a neural net trained against known microfungi.

35. The method according to claim 31 or claim 32, comprising performing a cluster analysis mapping of the sensor outputs.

36. The method according to claim 31 or 32, in which the detection region comprises an enclosed space above a Petri dish or other laboratory culture dish.

37. The method according to claim 31 or 32, in which the array of sensors is first purged using a purging gas.

38. The apparatus according to claim 8, wherein the microorganism is a microfungi.

39. The apparatus according to claim 38, in which the sensors comprise semi-conducting polymers, the resistance or impedance of which varies according to exposure to gases or vapors.

40. The apparatus according to claim 38 or claim 39, comprising a store for a library of responses to known microfungi and comparison means operable automatically to compare a given response against the library.

41. The apparatus according to claim 38 or claim 39, comprising a neural net, the input to which comprises the array of sensors and which is trained against known microfungi.

42. The apparatus according to claim 38 or claim 39, comprising a probe for sampling a detection region by abstracting gas or vapor from said region to be passed to said detector means.

43. The apparatus according to claim 42, said probe comprising a cover for enclosing a Petri or other laboratory culture dish or an area of growth medium thereon.

44. The apparatus according to claim 43, said probe comprising a carrier gas feed and return.

45. The apparatus according to claim 44, comprising a source of carrier gas.

46. The method according to claim 1, comprising detecting gas or vapor associated with the microorganism species and differentiating said gas or vapor from gas or vapor associated with other microorganism species.

47. The method according to claim 1, comprising detecting gas or vapor associated with a bacterial species and differentiating said gas or vapor from gas or vapor associated with other bacterial species.

48. The method according to claim 1, comprising detecting gas or vapor associated with a microfungi species and differentiating said gas or vapor from gas or vapor associated with other microfungi species.

* * * * *